US00PP28857P3

(12) United States Plant Patent
Wood

(10) Patent No.: US PP28,857 P3
(45) Date of Patent: Jan. 9, 2018

(54) ***PHYSOCARPUS* PLANT NAMED 'SMNPOTWG'**

(50) Latin Name: *Physocarpus opulifolius*
Varietal Denomination: SMNPOTWG

(71) Applicant: Timothy Wood, Spring Lake, MI (US)

(72) Inventor: Timothy Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 54 days.

(21) Appl. No.: 14/756,865

(22) Filed: Oct. 22, 2015

(65) Prior Publication Data

US 2017/0118889 P1 Apr. 27, 2017

(51) Int. Cl.
*A01H 5/00* (2006.01)

(52) U.S. Cl.
USPC ..... Plt./226

(58) Field of Classification Search
USPC ..... Plt./226
CPC ..... A01H 5/0216; A01H 5/00; A01H 5/02
See application file for complete search history.

(56) References Cited

U.S. PATENT DOCUMENTS

PP26,246 P2 * 12/2015 Verhoef ..... Plt./226

OTHER PUBLICATIONS

Spring Meadow Nursery, Inc. Flowering Shrubs Starter Plants Catalog and Shrub Reference 2015-2016, retrieved on Feb. 13, 2017, retrieved from the Internet at <http://springmeadownursery.com/content-media/catalog_2015.pdf> pp. 1-6, 24 and 78.*

* cited by examiner

*Primary Examiner* — June Hwu
(74) *Attorney, Agent, or Firm* — Cassandra Bright

(57) ABSTRACT

A new and distinct *Physocarpus* cultivar named 'SMNPOTWG' is disclosed, characterized by a small plant form, early flowering, smaller leaves, mildew resistance and abundant red-purple colored flowers, maturing to white. The new variety is a *Physocarpus*, normally produced as an outdoor garden or container plant.

2 Drawing Sheets

Latin name of the genus and species: *Physocarpus opulifolius.*

Variety denomination: 'SMNPOTWG'.

BACKGROUND OF THE INVENTION

The new *Physocarpus* cultivar is a product of a planned breeding program conducted by the inventor, Timothy D. Wood, in Grand Haven, Minn. The objective of the breeding program was to produce new *Physocarpus* varieties with unique foliage and powdery mildew resistance. The open pollenation resulting in this new variety was made during Summer of 2010.

The new *Physocarpus* 'SMNPOTWG' resulted from an open pollination in which seed was collected from an unnamed, unpatented proprietary seedling. Various *Physocarpus* were present in the field, making accurate identification of the pollen parent impossible. The new variety was identified as a potentially interesting selection in the Summer of 2013, at a commercial nursery in Grand Haven, Minn.

Asexual reproduction of the new cultivar 'SMNPOTWG' by softwood cuttings was first performed during the Summer of 2013, at commercial greenhouse in Grand Haven, Minn. Subsequent propagation has shown that the unique features of this cultivar are stable and reproduced true to type in 3 successive generations.

SUMMARY OF THE INVENTION

The cultivar 'SMNPOTWG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNPOTWG' These characteristics in combination distinguish 'SMNPOTWG' as a new and distinct *Physocarpus* cultivar:

1. Smaller plant size.
2. Smaller leaves.
3. Yellow-Green leaves.
4. Good mildew resistance.
5. Flowering at a younger age.
6. Good performance in containers.
7. Abundant flowers, opening Red-purple, maturing to almost entirely white.

PARENT COMPARISON

Plants of the new cultivar 'SMNPOTWG' are similar to plants of the parent, in most horticultural characteristics, however, plants of the new cultivar 'SMNPOTWG' differ in the following:

1. Improved resistance to mildew.
2. Flowers at a younger age than the parent variety.
3. 'SMNPOTWG' is a dwarf, the parent is full sized.
4. The new variety has Yellow-Green foliage, the parent has yellow foliage with red new growth.

COMMERCIAL COMPARISON

Plants of the new cultivar 'SMNPOTWG' can also be compared to the commercial variety *Physocarpus opulifo-*

*lius* 'Bert Dart's G' U.S. Plant Pat. No. 26,246. The varieties are similar in most horticultural characteristics; however 'SMNPOTWG' differs in the following:

1. The new variety is a dwarf plant, this comparator is a semi-dwarf.
2. The new variety has smaller leaves than this comparator.
3. The new variety blooms more consistently and abundantly at a younger age than this comparator.

BRIEF DESCRIPTION OF THE PHOTOGRAPHS

Figure 1:
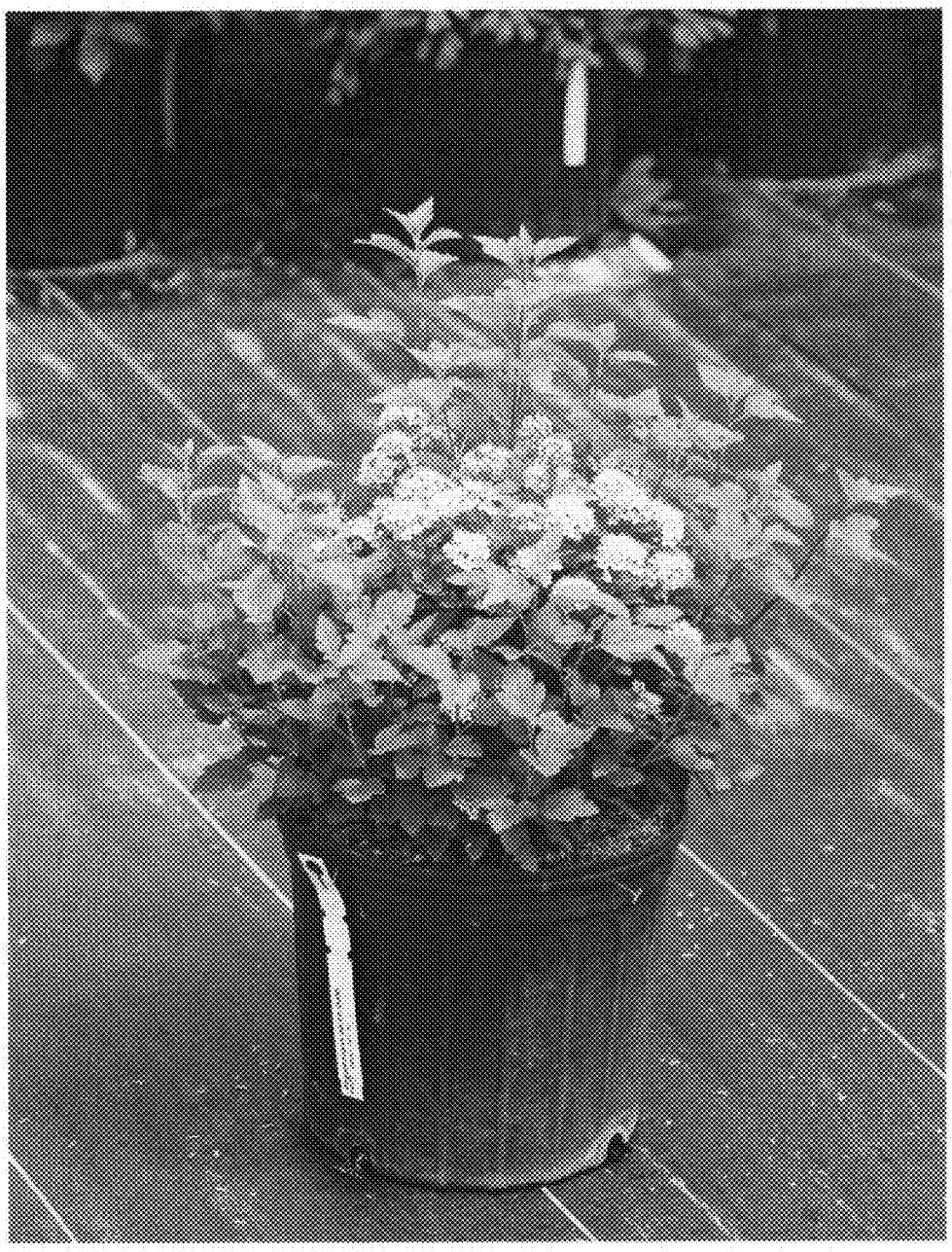

The accompanying photograph in FIG. 1 illustrates in full color a typical 2 year old plant of 'SMNPOTWG' grown in a 2 gallon container.

Figure 2:
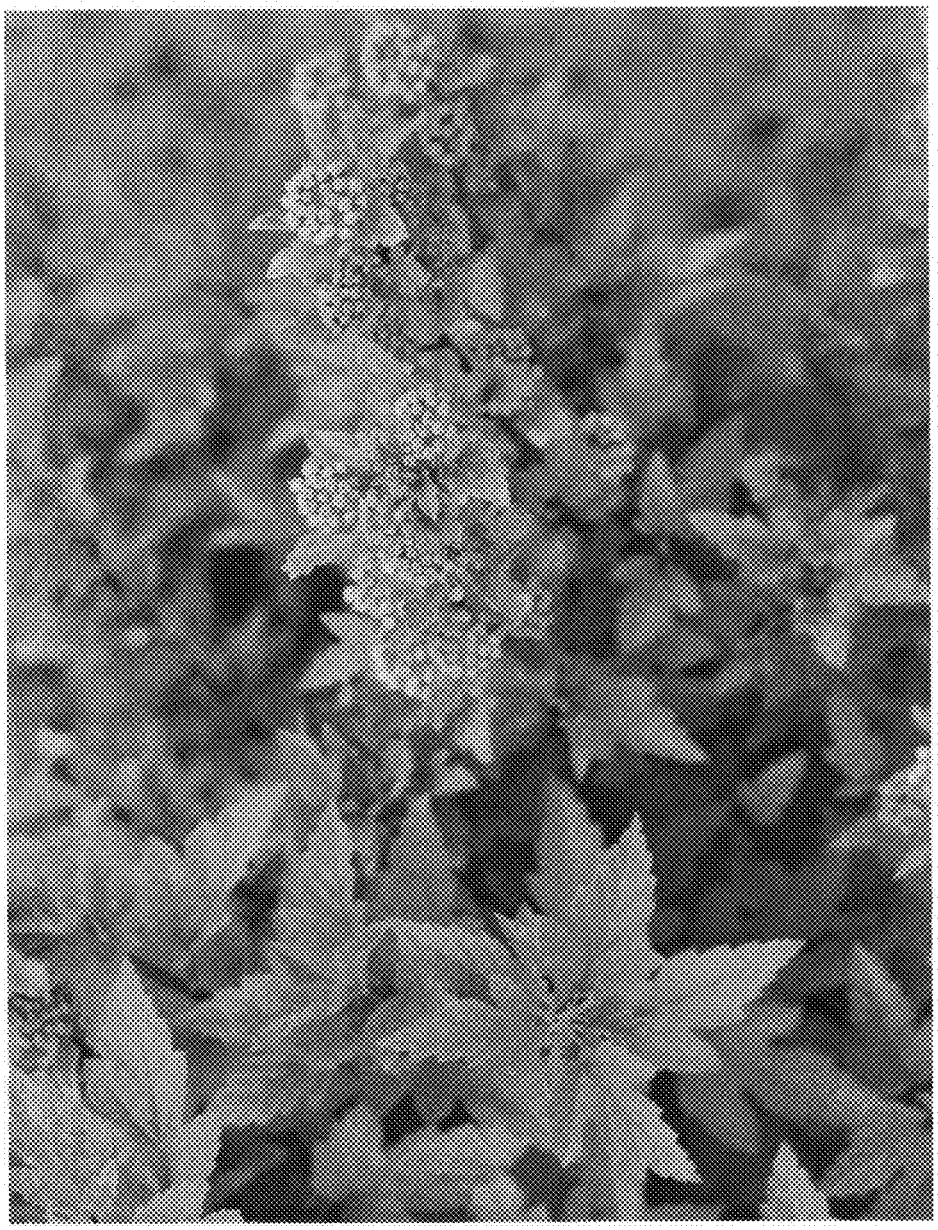

FIG. 2 illustrates in full color a typical inflorescence and foliage of 'SMNPOTWG' grown outdoors in Grand Haven, Minn., in a garden setting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SMNPOTWG' plants grown outdoors in Grand Haven, Minn. This occurred during June of 2014. The plants were approximately 2 years old grown in 2 gallon containers. The growing temperature ranged from 18° C. to 27° C. during the day, and 5° to 10° C. at night. The field is un-shaded, giving bright, normal sunlight conditions. Measurements and numerical values represent averages of typical plant types.

Botanical classification: *Physocarpus opulifolius* 'SMNPOTWG'.

PROPAGATION

Time to initiate roots: About 24 days at approximately 25° C.

Root description: Fine, and freely branching, both fibrous and fleshy.

Time to produce a liner: About 60 days at 24° C.

PLANT

Plant type: Shrub perennial.

Age of plant described: Approximately 2 years old.

Growth habit: Upright, rounded.

Pot size of plant described: 2 gallon pot.

Height: Approximately 28 cm to top of foliage.

Plant spread: Approximately 40 cm.

Growth rate: Moderate.

Plant vigor: Strong.

Branching characteristics: Free, basal branching when pinched.

Length of primary lateral branches: Approximately 20-30 cm.

Diameter of lateral branches: Approximately 0.3 cm.

Quantity of lateral branches: Minimum average 50.

Stem:

- *Appearance*.—Rounded, slight pentagonal shape.
- *Aspect/angle*.—Some 20° others 90°.
- *Strength*.—Strong.
- *Texture*.—Glabrous to date. Bark exfoliation expected to occur with further age.
- *Stem color*.—Near RHS Yellow-Green 144B.
- *Bark color*.—Near RHS Brown 200D.

Internode length: Average range 2 to 3 cm.

FOLIAGE

Leaf:

- *Arrangement*.—Alternate, single.
- *Average length*.—Approximately 4.5 cm.
- *Average width*.—Approximately 3.4 cm.
- *Shape of blade*.—Broad ovate. Tri-lobed.
- *Apex*.—Acute.
- *Base*.—Rounded.
- *Attachment*.—Stalked.
- *Margin*.—Serrate-dentate.
- *Texture of top surface*.—Smooth.
- *Texture of bottom surface*.—Smooth.
- *Pubescence*.—None.
- *Color*.—Young foliage upper side: Near RHS Green 144C, youngest foliage flushed Greyed-Orange 166B and N167C. Young foliage under side: Near RHS Green 144C. Mature foliage upper side: Near RHS Green 143C. Mature foliage under side: Near RHS Green 139C. Late Summer/Early Fall upper side: Near RHS Green 143B flushed Yellow-Green N144A. Late Summer/Early Fall under side: Near RHS Green 143C flushed Yellow-Green N144B.
- *Venation*.—Type: Palmate. Venation color upper side: Near RHS Green 143C. Venation color under side: Near RHS Green 139C.
- *Petiole*.—Average Length: Approximately 1.7 cm. Diameter: Approximately 0.1 cm. Petiole color upper side: Near RHS Green 143C. Petiole color lower side: Near RHS Green 144B. Petiole Texture upper side; Glabrous, two ridges run on the edges of the petiole. Petiole Texture lower side; Glabrous.
- *Stipule*.—Highly reduced, less than 2 mm, insignificant.

FLOWER

Natural flowering season: May-June.

Inflorescence type and habit: Terminal and axillary rounded cyme.

Quantity of flowers per inflorescence: Average range 31 to 40.

Inflorescence size:

- *Width*.—Approximately 3.5 cm.
- *Height*.—Approximately 2.8 cm.

Quantity of flowers per lateral stem: 200 to 800.

Quantity of flowers per plant: 2000 to 8000.

Individual flowers:

- *Flower form*.—Single whorl of five petals.
- *Flower aspect*.—Upright and outward.
- *Size*.—Diameter: Approximately 0.7 cm. Length: Approximately 0.5 cm. Depth: Approximately 0.4 cm. Persistence: Persistent.

Petal:

- *Petal arrangement*.—Whorl.
- *Number of petals per flower*.—5.
- *Petal appearance*.—Matte.
- *Petal shape*.—Obovate.
- *Margin*.—Entire.

*Tip shape*.—Obovate.
*Length*.—0.3 cm.
*Width*.—0.2 cm.
*Texture*.—Upper: Glabrous. Lower: Glabrous.

Petal color:
*When opening*.—Upper surface: Outer edge near RHS Red-Purple 63C; rest near RHS White 155D. Lower surface: Outer edge near RHS Red-Purple 63C; rest near RHS White 155D.
*Fully opened*.—Upper surface: Near RHS White 155D. Lower surface: Near RHS White 155D.
*Fading*.—Upper surface: Near RHS White 155A. Lower surface: Near RHS White 155A.

Petaloids: None present.

Bud:
*Shape*.—Globose.
*Length*.—Approximately 0.3 cm.
*Diameter*.—Approximately 0.3 cm.
*Color*.—Variable. Most commonly Near RHS White 155D, with heavy streaking near RHS Red-Purple 62B. Less commonly White 155D with very little Red-Purple streaking.

Sepals:
*Shape*.—Triangular.
*Number of sepals*.—4.
*Arrangement*.—Whorl.
*Length*.—Approximately 0.2 cm.
*Width*.—Approximately 0.15 cm.
*Margin*.—Entire.
*Base*.—Connected, Obtuse.
*Tip*.—Acuminate.
*Texture*.—Pubescent.
*Color*.—Immature: Near RHS Yellow-Green 144B. Mature: Near RHS Yellow-Green 145C.

Peduncle:
*Length*.—Average 2.0 cm.
*Diameter*.—0.2 cm.
*Color*.—Near RHS Yellow-green 144B.
*Orientation*.—60° from stem, straight.
*Strength*.—Good.
*Texture*.—Glabrous.

REPRODUCTIVE ORGANS

Stamens:
*Number*.—20.
*Filament length*.—Approximately 0.2 cm.
*Filament color*.—Near RHS White 155A.

Anthers:
*Shape*.—Globose.
*Length*.—Less than 0.1 cm.
*Color*.—Immature: Near RHS Red-Purple 58D. When Fading: Near RHS Greyed-Orange 177A.
*Pollen*.—Some.
*Pollen color*.—Near RHS White 155A.

Pistil:
*Number*.—Average of 4.
*Length*.—Approximately 0.3 cm.
*Style*.—Length: Approximately 0.3 cm. Color: Near RHS White 155B.
*Stigma*.—Shape: Club-shaped. Color: Near RHS Yellow-green 153D. Ovary color: Near RHS Yellow-Green 151D.

OTHER CHARACTERISTICS

Seeds and fruits: Three lobed chambers, overall 3 mm tall, 2 mm in diameter. Colored near RHS Red-Orange N34D. Seed spherical, less than 0.5 mm in diameter, colored near Orange-White 159A.

Garden performance: Very good.

Disease/pest resistance: Good resistance to Powder Mildew. Neither resistance nor susceptibility to pests common to *Physocarpus* have been observed. Many Genus and species of powdery mildew are found on *Physocarpus*. The inventor cannot accurately identify which powdery mildew the new variety is resistant to.

Temperature tolerance: The new variety tolerates temperatures between −31 to 38° C.

What is claimed is:

1. A new and distinct cultivar of *Physocarpus* plant named 'SMNPOTWG' as herein illustrated and described.

* * * * *